Figure 1:
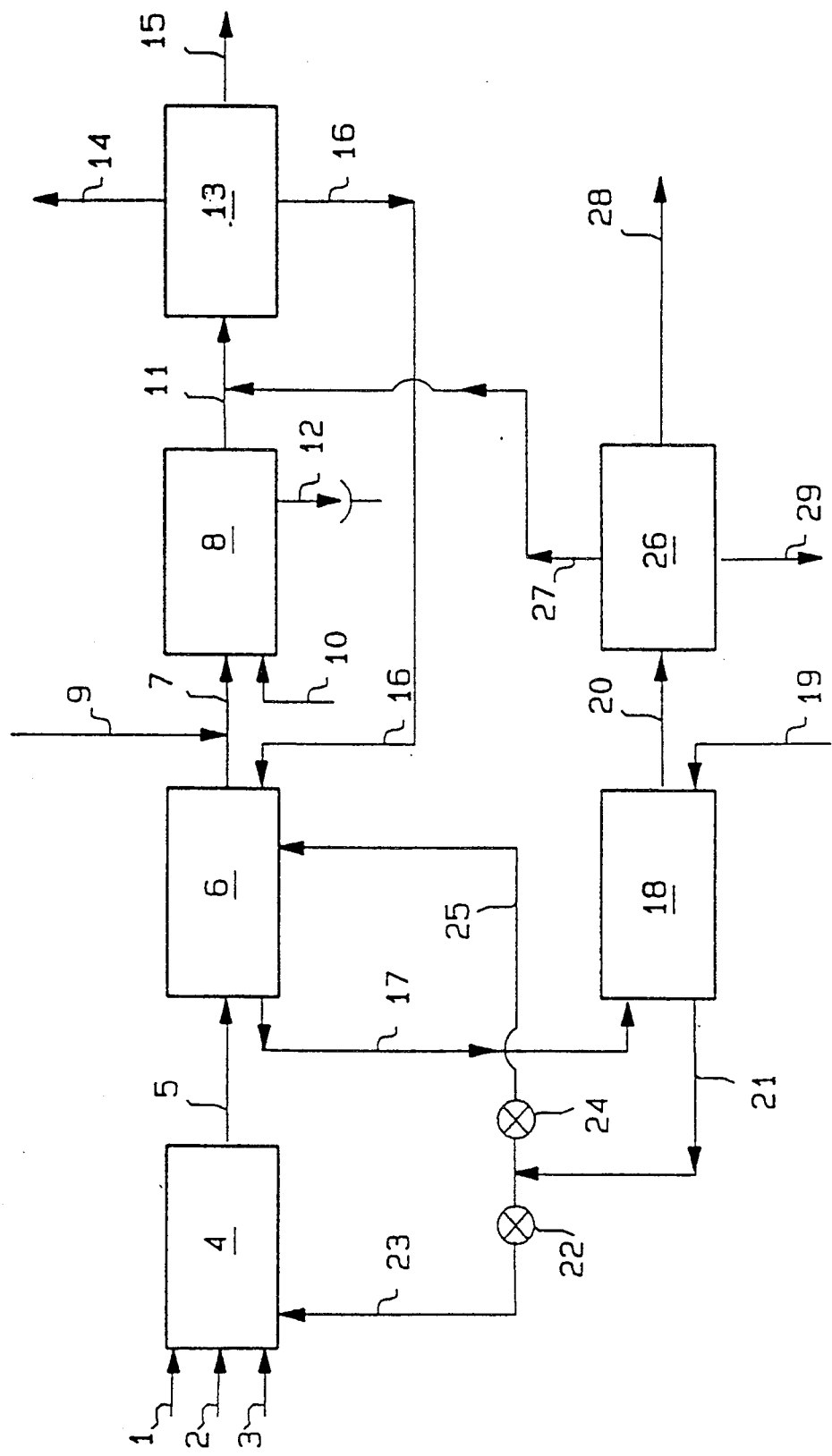

United States Patent [19]
Grunchard

[11] Patent Number: 5,344,945
[45] Date of Patent: Sep. 6, 1994

[54] PROCESS FOR THE PRODUCTION OF EPICHLOROHYDRIN

[75] Inventor: Frans Grunchard, Overijse, Belgium

[73] Assignee: Solvay (Société Anonyme), Brussels, Belgium

[21] Appl. No.: 30,559

[22] Filed: Mar. 12, 1993

[30] Foreign Application Priority Data

Mar. 17, 1992 [BE] Belgium .............................. 09200259

[51] Int. Cl.⁵ ...................... C07C 29/86; C07C 31/34; C07D 301/26; C07D 303/08
[52] U.S. Cl. ..................................... 549/521; 568/847
[58] Field of Search .................. 568/847; 549/521, 541

[56] References Cited

U.S. PATENT DOCUMENTS 2,714,123 7/1955 Johnson ............................... 568/847
3,061,615 10/1962 Viriot et al. ......................... 549/541
4,900,849 2/1990 Saletan ................................ 568/847

FOREIGN PATENT DOCUMENTS 1158953 12/1963 Fed. Rep. of Germany ...... 549/521
50/028408 9/1975 Japan .
789479 12/1980 U.S.S.R. .
985405 5/1962 United Kingdom ................ 549/521

*Primary Examiner*—Joseph E. Evans
*Attorney, Agent, or Firm*—Spencer, Frank & Schneider

[57] ABSTRACT

Process for the production of epichlorohydrin in which the chloroaliphatic impurities formed at the hypochlorination of allyl chloride to dichloropropanols are removed from the crude aqueous solution of dichloropropanols before dehydrochlorination, by extraction with a recycled organic solvent which is rich in 1,2,3-trichloropropane.

6 Claims, 1 Drawing Sheet

PROCESS FOR THE PRODUCTION OF EPICHLOROHYDRIN

The present invention relates to a process for the production of epichlorohydrin by dehydrochlorination of dichloropropanols, themselves obtained by hypochlorination of allyl chloride, and, more particularly, to an improved process in which the aqueous effluents are impoverished in chlorinated organic impurities.

It is well known to prepare epichlorohydrin by dehydrochlorination, with the aid of a basic compound, of an aqueous solution of dichloropropanols, which solution is obtained by reacting allyl chloride, water and chlorine in a suitable reaction zone.

During the hypochlorination reaction of allyl chloride to dichloropropanols, many undesirable by-products are generally formed. It is possible to improve the selectivity of the hypochlorination reaction by carrying out the reaction in very dilute aqueous medium. This commonly used practice causes, however, in the subsequent dehydrochlorination stage of the dichloropropanols to epichlorohydrin, the formation of significant volumes of aqueous effluents containing organic impurities in the highly diluted state, the purification of which requires expensive treatments. These organic impurities consist, inter alia, of heavy chlorinated organic products which are difficult to remove and which have the by-products of the hypochlorination reaction as precursors. A reduction in the quantity of chlorinated organic impurities present in the aqueous effluents would enable significant cost savings to be achieved.

Patent Application EP-A-0,359,331 from Shell discloses a process for reducing the content of chloroalkanes and chloroaliphatic ethers in an aqueous solution of dichloropropanols by bringing this solution into contact with tetrachloromethane. After separation of the aqueous phase, the solvent, which is laden with impurities, is washed with water in order to remove therefrom the dichloropropanols which were also extracted, is then regenerated by distillation and recycled to the extraction stage. This known process has the disadvantage of necessarily containing a stage for regenerating the solvent used, resulting in an increase in energy consumption. Moreover, a certain fraction of the solvent is inevitably lost at various stages of the process, consequently implying the regular addition of fresh solvent in order to preserve an adequate volume ratio between the extraction solvent and the crude aqueous solution of dichloropropanols to be treated. This process additionally implies the use of a product external to the process and it requires additional stages for reconversion of epichlorohydrin to dichloropropanols.

In U.S. Pat. No. 2,873,298 from Shell, the majority of the aqueous product of hypochlorination of allyl chloride to dichloropropanols is conveyed, with a slight excess of sodium hydroxide, into a steam distillation column. The crude epichlorohydrin solution obtained by dehydrochlorination, which contains trichloropropane and unidentified organic impurities, is diluted with the balance of the aqueous dichloropropanols solution. This diluted solution is subjected to settling. The organic phase which contains the majority of the trichloropropane and unidentified organic impurities, as well as appreciable amounts of epichlorohydrin and dichloropropanols, is subjected to a stage for converting epichlorohydrin to monochlorohydrin or to a stage for distilling epichlorohydrin. These stages are followed by the recovery of mono- and/or dichloropropanols by extracting with water and the residual organic phases, then mainly containing trichloropropane and the unidentified organic impurities, are discarded. This process does not improve the quality of the aqueous effluents from the stage of dehydrochlorination of the dichloropropanols to epichlorohydrin.

The invention is aimed at remedying the disadvantages of the known processes for the preparation of epichlorohydrin by providing a process for the preparation of epichlorohydrin starting from allyl chloride, via the dichloropropanols, containing a purification stage of the crude aqueous solution of dichloropropanols by liquid/liquid extraction by means of a markedly more efficient extraction solvent than tetrachloromethane. The yields are very good, the process is simple to carry out and it makes it possible to reduce energy consumption. The direct aqueous effluents from the process contain very few chlorinated organic impurities, which makes it possible to avoid certain subsequent stages, which are too complex or which consume too much energy, in order to purify them before discarding them. The purity of the epichlorohydrin obtained is very well suited to subsequent uses of the product without additional expensive and energy-consuming stages being necessary. Additionally, the chlorinated organic impurities are concentrated and can consequently be treated economically, either with a view to subsequently enhancing their value or with a view to removing them.

Consequently, the invention relates to a process for the production of epichlorohydrin starting from allyl chloride, comprising a hypochlorination stage of the allyl chloride to form a crude aqueous solution of dichloropropanols, a purification stage of the crude aqueous solution of dichloropropanols from chlorinated organic impurities in order to forth a purified aqueous solution of dichloropropanols, and a hydrolysis stage of the dichloropropanols, characterized in that the purification of the crude aqueous solution of dichloropropanols is carried out by extraction by means of a recycled organic extraction solvent which is rich in 1,2,3-trichloropropane.

The chlorinated organic impurities present in the crude aqueous solution of dichloropropanols obtained by hypochlorination of allyl chloride to dichloropropanols essentially comprise, on the one hand, chlorinated alkanes, mainly 1,2,3-trichloropropane and, on the other hand, other impurities hereafter called chloroaliphatic impurities, which mainly comprise chloroaliphatic ethers such as, in particular, polychlorodipropyl ethers, polychloro(hexyl propyl ethers), and polychloro(nonyi propyl ethers), and chloroaliphatic alcohols such as, in particular, polychlorohexanols or -diols and polychlorononanols.

Organic solvent rich in 1,2,3-trichloropropane is understood to mean, for the purposes of the present invention, a solvent comprising at least approximately 30% by weight of 1,2,3-trichloropropane. Preferably, this recycled organic solvent comprises at least approximately 50% by weight of 1,2,3-trichloropropane. Although the process according to the invention can use a recycled organic solvent consisting solely of 1,2,3-trichloropropane, in practice the recycled organic extraction solvent used is a mixture of products which can comprise up to approximately 95% of 1,2,3-trichloropropane, the balance consisting of various compounds commonly used or formed during the synthesis of epichlorohydrin from allyl chloride. The nature of the compounds other than 1,2,3-trichloropropane present in the recycled organic solvent and their content depend on the embodiment of the process according to the invention. As a general rule, these compounds are mainly dichloropropanols. The recycled organic solvent can comprise from 0.5 to 60% by weight of dichloropropanols.

The recycled organic solvent can also optionally comprise slight amounts of epichlorohydrin, for example from 0.1 to 5% by weight, and small amounts of chloroaliphatic impurities, for example from 0.1 to 5% by weight.

The process according to the invention appears particularly advantageous. In effect, the majority of the chloroaliphatic impurities present in the crude aqueous solution of dichloropropanols are markedly more soluble in 1,2,3-trichloropropane than in the extraction solvents used in the known processes, such as tetrachloromethane. 1,2,3-trichloropropane consequently proves to be a particularly efficient solvent for extracting the chloroaliphatic impurities such as the chloroaliphatic ethers and alcohols present in the crude aqueous solution of dichloropropanols. Bringing the crude aqueous of dichloropropanols into contact with a recycled organic solvent which is rich in 1,2,3-trichloropropane leads, after extraction, to a purified aqueous solution dichloropropanols which is highly impoverished in chloroaliphatic impurities, particularly chloroaliphatic ethers and alcohols.

with respect to the known process using an extraction solvent such as tetrachloromethane, the purified aqueous solution of dichloropropanois obtained in the process according to the invention contains larger amounts of 1,2,3-trichloropropane- surprisingly, the presence of these amounts of 1,2,3-trichloropropane has practically no effect, at the subsequent dehydrochlorination stage of the dichloropropanols, on the content chlorinated organic impurities in the aqueous effluents, which are thus, taken as a whole, highly purified from chlorinated organic impurities generated at the nypochlorination stage of the allyl chloride.

As 1,2,3-trichloropropane is usually produced in not insignificant amounts during the hypochlorination allyl chloride to dichloropropanols, the existing processes generally have a device intended for recovering and purifying 1,2,3-trichloropropane with a view to subsequently enhancing its value. Most often, the purification of 1,2,3-trichloropropane is carried out distillation. The recycling of at least a part of a flow containing 1,2,3-trichloropropane resulting from such a distillation with a view to using it as an extraction solvent for chlorinated organic impurities present in the crude aqueous solution of dichloropropanols consequently requires no additional investment and practically no increase in energy consumption. The process according to the invention additionally has the advantage of carrying out in a single stage, consisting of a fractional distillation, the purification of the 1,2,3-trichloropropane by-product, the regeneration of the extraction solvent to be recycled and the concentration, with a view to their destruction, of the chloroaliphatic impurities extracted from the crude aqueous solution of dichloropropanols.

In a preferred embodiment of the process according to the invention, epichlorohydrin is prepared according to a process comprising the following stages:
a) hypochlorination of allyl chloride to form a crude aqueous solution of dichloropropanols which additionally contains small amounts of chlorinated organic impurities, especially 1,2,3-trichloropropane and chloroaliphatic impurities.
b) extraction of this aids aqueous solution of dichloropropanols with a recycled organic extraction solvent, which is rich in 1,2,3-trichloropropane, in an amount sufficient to obtain an organic phase which mainly comprises 1,2,3-trichloropropane enriched in chloroaliphatic impurities and an aqueous phase containing the majority of the dichloropropanols, highly impoverished in chloroaliphatic impurities.
c) dehydrochlorination of the dichloropropanols to epichlorohydrin by introduction of a basic compound into the aqueous phase obtained in stage b)., steam distillation of the epichlorohydrin foraged to obtain crude epichlorohydrin and discarding of the aqueous effluents.
d) separation, by fractional distillation, of the crude epichlorohydrin formed in c) into a light fraction, into an intermediate fraction consisting of purified and recycling of the residual heavy fraction from this distillation to the extraction stage b) where it at least partially constitutes the recycled organic extraction solvent rich in 1,2,3-trichloropropane.
e) washing of the organic phase obtained in stage b) with water to obtain, after separation of the phases, a washing water containing the majority of the dichloropropanols present in the said organic phase and a washed organic extract, containing markedly less dichloropropanols than as supplied, the washing water laden with dichloropropanols being recycled to at least one of the a) hypochlorination, b) extraction or c) dehydrochlorination stages.
f) separation, by fractional distillation, of the said washed organic extract from stage e) into a head cut conveyed to the separation stage d) of the crude epichlorohydrin by distillation, into a middle cult consisting of purified 1,2,3-trichloropropane and into a bottom cut consisting essentially of the chloroaliphatic impurities.

This preferred embodiment of the process makes it possible to discharge from the process the products lighter than epichlorohydrin which may be present in the washed organic extract, without having to resort to an additional purging. Additionally, the 1,2,3-trichloropropane contained in the head cut obtained in stage f) by separation by distillation of the washed organic extract and conveyed to separation stage d) the crude epichlorohydrin by distillation constitutes, with the unconverted dichloropropanols and with the 1,2,3-trichloropropane dissolved in the aqueous phase extraction stage b), virtually all the residual head fraction from the separation of the crude epichlorohydrin by distillation carried out in stage d), which residual heavy fraction is recycled to extraction stage b), where it constitutes, in this preferred embodiment of the process according to the invention, the recycled organic extraction solvent, rich in 1,2,3-trichloropropane, which is brought into contact with the crude aqueous solution. of dichloropropanols. Such an arrangement makes possible an optimum recovery of all the products and reactants taking part in the process for the preparation of epichlorohydrin. Additionally, with respect to the known processes mentioned above, this preferred embodiment of the process according to the invention has the additional advantage of not containing a reconversion stage of epichlorohydrin to dichloropropanols.

In a variation of this preferred embodiment of the process according to the invention, part of the purified 1,2,3-trichloropropane, corresponding to the middle cut obtained in the separation stage f) by distillation of the washed organic extract, can be added to the residual heavy fraction obtained in the separation stage d) of the crude epichlorohydrin by distillation, the mixture obtained being recycled to the extraction stage b) as recycled organic extraction solvent.

In a particularly preferred way, the separation by distillation of the washed organic extract of stage e), carried out in stage f), is carried out such that the head cut conveyed to the separation stage d) of the epichlorohydrin by distillation contains from 50 to 98% of 1,2,3-trichloropropane, the balance consisting of lighter compounds than 1,2,3-trichloropropane. The compounds lighter than 1,2,3-trichloropropane, that is to say those with a boiling point at normal pressure of less than 156° C., mainly comprise certain products such as impurities present in the allyl chloride and unreacted allyl chloride from the hypochlorination.

This particularly preferred embodiment of the process according to the invention is described below in detail, reference being made to FIG. 1, which represents schematically the preferred arrangement of the various stages.

Allyl chloride, chlorine and water, introduced respectively via the pipes 1, 2 and 3, react in the reaction zone 4 to form, by hypochlorination of the allyl chloride, dichloropropanols as well as small amounts of many chlorinated organic impurities. The reaction zone 4 consists of one or a number of reactors which are consecutive or arranged in parallel, such as stirred reactors, recirculation reactors, Venturi reactors or any other type of reactor which makes possible a rapid and efficient dispersion of the reactants. The hypochlorination reaction generally takes place at a temperature from 20° to 70° C.

The crude aqueous solution of dichloropropanols, generally containing from 2 to 12% by weight of dichloropropanols and the chlorinated organic impurities, is conveyed, via the pipe 5, to an extraction zone 6 where it is brought into intimate contact with a recycled organic extraction solvent which is rich in 1,2,3-trichloropropane, introduced via the pipe 16. The crude aqueous solution of dichloropropanols and the extraction solvent are brought into contact in one or a number of stages, by means of any conventional device for liquid/liquid extraction, for example by bringing into intimate contact by means of a stirred reactor, a rotary disc extractor, a centrifugation extractor or a perforated plate column, operating either counter-current-wise or co-current-wise. Extraction can be carried out continuously or noncontinuously. Preferably, it is carried out continuously. In this case, the ratio between the flow rate of the extraction solvent rich in 1,2,3-trichloropropane, introduced via 16, and the flow rate of the crude aqueous solution of dichloropropanols, introduced via the pipe 5, necessary for carrying out a satisfactory extraction of the chloroaliphatic impurities, and more particularly of the chloroaliphatic ethers and alcohols, of course depends on various parameters, especially the liquid/liquid extraction device used and the content of 1,2,3-trichloropropane in the extraction solvent. Generally, it may be asserted however that good results can be obtained when this ratio is greater than approximately 0.001. This ratio is preferably greater than approximately 0.002. In particular, it is preferably greater than approximately 0.005. Generally, this ratio is less than approximately 0.1. It is preferably less than approximately 0.05. In particular, it is preferably less than approximately 0.03.

Depending on the extraction device used, it may be necessary to separate the mixture containing an aqueous phase and an organic phase into these two respective phases. This separation can be carried out simply by settling, but it is also possible to use any other conventional device for separating phases, such as centrifugation or separation by a hydrocyclone. The organic phase mainly comprises 1,2,3-trichloropropane enriched in chloroaliphatic impurities, but also contains a not insignificant amount of dichloropropanols. Its composition most often corresponds to the equilibrium composition, determined by the partition coefficients of the various compounds between water and 1,2,3-trichloropropane. The aqueous phase contains most of the dichloropropanols. It is generally saturated in 1,2,3-trichloropropane. It constitutes, in the process according to the invention, the purified aqueous solution of dichloropropanols. The aqueous phase obtained in the extraction zone 6 is particularly highly purified from chloroaliphatic impurities. It has an extremely low residual content of these impurities, which is impossible to achieve solely by the known processes mentioned above The aqueous phase, purified from chloroaliphatic impurities, leaves the extraction zone 6 via the pipe 7 and is then treated with an aqueous alkaline solution introduced via the pipe 9, which neutralizes the hydrochloric acid formed during hypochlorination and which causes, by dehydrochlorination, the conversion of the dichloropropanols to epichlorohydrin. As alkaline aqueous solution, there may be especially used a solution of sodium hydroxide, calcium hydroxide or else sodium carbonate.

The solution obtained is then immediately transferred into a steam distillation column 8, supplied at its base with a steam flow 10. The epichlorohydrin, as well as the 1,2,3-trichloropropane solubilized in the aqueous phase at the extraction stage 6, the residual chloroaliphatic impurities not extracted from the aqueous phase in the extraction zone 6 and certain relatively volatile compounds, generated especially during the dehydrochlorination of the dichloropropanols, are entrained by the steam into the top of the steam distillation column 8. After condensation of the entrained products, the latter settle into two phases (not represented in FIG. 1): a less dense aqueous fraction, containing part of the unconverted dichloropropanols and a small amount of epichlorohydrin, which aqueous fraction is returned as reflux to the steam distillation column, and an organic fraction constituting the crude epichlorohydrin conveyed via the pipe 11 towards the distillation zone of the epichlorohydrin 13. This crude epichlorohydrin mainly contains, besides epichlorohydrin, a small amount of water, unconverted dichloropropanols, the 1,2,3-trichloropropane dissolved in the aqueous phase in the extraction zone 6 and the residual chloroaliphatic impurities which were not extracted from the aqueous phase in the extraction zone 6.

The aqueous effluents, containing especially the inorganic salts generated by the hydrolysis, are discharged at the foot of the column 8 via the pipe 12. The load of chloroaliphatic impurities generated in the hypochlorination stage of the allyl chloride is particularly low in these effluents, which makes their purification easier.

The distillation zone 13, consisting of one or, preferably, of a number of distillation columns, makes it possible to remove from the crude epichlorohydrin transported via the pipe 11, on the one hand, a light fraction comprising water and the relatively volatile compounds, which are discharged via the pipe 14 towards a treatment unit where they are generally destroyed, for example by combustion, and, on the other hand, a residual heavy fraction consisting mainly of 1,2,3-trichloropropane, unconverted dichloropropanols and chloroaliphatic impurities which were not extracted from the aqueous phase in the extraction zone 6. Recycled to the extraction zone 6 via the pipe 16, this heavy fraction constitutes, in this preferred embodiment of the process according to the invention, the recycled organic extraction solvent rich in 1,2,3-trichloropropane- The recycling of this heavy fraction additionally makes it possible to recover the dichloropropanols possibly not hydrolyzed during the dehydrochlorination stage and entrained in the crude epichlorohydrin. As a general rule, this heavy fraction may comprise, besides 1,2,3-trichloropropane, from 0.5 to 60% by weight of dichloropropanols and from 0.1 to 5% of chloroaliphatic impurities. Preferably, it comprises from 1 to 40% dichloropropanols and from 0.5 to 3% of chloroaliphatic impurities.

The purified epichlorohydrin, for its part, leaves the process via the pipe 15.

The organic phase obtained in the extraction zone 6 mainly contains 1,2,3-trichloropropane arising, on the one hand, from the recycled organic extraction solvent introduced at the extraction stage 6 via the pipe 16 and, on the other hand, formed during the hypochlorination of the allyl chloride in the reaction zone 4, and the chloroaliphatic impurities, the chloroaliphatic ethers and alcohols of which are also formed during the hypochlorination of the allyl chloride. The organic phase, however, also contains not insignificant amounts of dichloropropanols extracted from the crude aqueous solution of dichloropropanols by the organic extraction solvent during the extraction stage 6, as well as small amounts of products such as the impurities from the allyl chloride and, possibly, allyl chloride which was not converted in the reaction zone 4.

In order to recover the dichloropropanols present the organic phase obtained in the extraction zone this organic phase is transferred via the pipe 17 into a washing zone 18 where it is washed with water. In this zone 18, the washing is carried out in one or a number of stages in any conventional liquid/liquid extraction device, by bringing the organic phase conveyed via the pipe 17 into intimate contact with water, which introduced into the zone 18 via the pipe 19. The amount of water necessary for carrying out this washing depends on the efficiency of the device used. This washing can be carried out continuously or noncontinuously. Preferably, it is carried out continuously. In this case, the volume ratio between the flow of washing water and the flow of organic extract is generally between 5:1 and 20:1. After washing and separating the phases, the washing water is generally saturated with 1,2,3-trichloropropane and it can contain from 1 to 10% by weight of dichloropropanols. It is conveyed, via the pipe 21, the valve 22 and the pipe 23 to the reaction zone 4, where it can replace part of the water introduced via the pipe 3. If the dichloropropanols content of this washing water is sufficiently high, it is preferably conveyed directly to the extraction zone 6 via the pipe 21, the valve 24 and the pipe 25.

At the outlet of the zone 18, the washed organic extract contains practically no more dichloropropanols. It mainly comprises 1,2,3-trichloropropane and generally from 3 to 25% of chloroaliphatic impurities. This washed organic extract is transferred via the pipe 20 into the distillation zone 26. In this zone, comprising one or a number of fractional distillation stages, the washed organic extract is separated into a head cut containing 1,2,3-trichloropropane and the compounds which are lighter than 1,2,3-trichloropropane, which head cut is transported, via the pipes 27 and 11, to the distillation zone of epichlorohydrin 13, into a middle cut consisting of 1,2,3-trichloropropane with a purity of the order of 99%, which middle cut leaves the process via the pipe 28, and into a bottom cut consisting essentially of the chloroaliphatic impurities, which bottom cut is discharged via the pipe 29. Obtained in this way in a concentrated form, the chloroaliphatic impurities can be removed economically by various known techniques, for example by combustion.

In the particularly preferred embodiment of the process according to the invention illustrated in FIG. 1, the distillation carried out in 26 is carried out such that the head cut recovered via the pipe 27 contains at feast approximately 50% of 1,2,3-trichloropropane. In a very particularly preferred way, its 1,2,3-trichloropropane content is greater than approximately 70%. Very good results have been obtained with a 1,2,3-trichloropropane content in this head cut of the order 80 to 98%. Besides 1,2,3-trichloropropane, this head cut mainly comprises the compounds which are lighter than 1,2,3-trichloropropane, mainly certain products such as the impurities present in the allyl chloride and allyl chloride which did not react during the hypochlorination.

The invention also relates to a process for the extraction of the chloroaliphatic impurities from a crude aqueous solution of dichloropropanols obtained by hypochlorination of allyl chloride, characterized in that the extraction is carried out by means of a recycled organic extraction solvent which is rich in 1,2,3-trichloropropane.

The invention also relates to the aqueous solution of dichloropropanols, which is highly purified from chloroaliphatic impurities, obtained by the process of the invention.

The invention finally relates to the use of a recycled extraction solvent which is rich in 1,2,3-trichloroaliphatic as an agent for the extraction or chloroaliphatic impurities contained in a crude solution of dichloropropanols, The following example illustrates the efficiency of the purification of the crude aqueous solution of dichloropropanols according to the process the invention by comparison with a known process.

Example

A crude aqueous solution of dichloropropanols, obtained by hypochlorination of allyl chloride, is first of all settled in order to remove therefrom the fraction of the chlorinated organic impurities which is easy to separate.

The table gives the concentration of various chloroaliphatic impurities present in the aqueous phase after settling, identified by their empirical formula, the various isomers being distinguished by their retention time in gas phase chromatography.

One liter of this settled aqueous phase is extracted at 50° C. with 25 ml of 1,2,3-trichloropropane (according to the invention), and another Liter with 25 ml of tetrachloromethane by way of comparison.

The table gives, for each extraction solvent used, the calculated partition coefficient between the organic phase and the aqueous phase, that is to say the ratio between the concentration of each impurity in the organic phase and its concentration in the aqueous phase, after extraction.

When, after extraction, the concentration c,f an impurity in the aqueous phase is less than the analytical detection limit, the minimum value of the partition coefficient is shown, corresponding to the ratio between the concentration of this impurity in the organic solvent and its detection limit in the aqueous phase. In this case, the value is preceded by the sign >.

TABLE

| Constituent (Empirical formula) | VPC Retention Time (minutes) | Initial content (mg/L) | Partition coefficients | |
|---|---|---|---|---|
| | | | Extraction with trichloropropane | Extraction with CCl$_4$ |
| C$_6$H$_{11}$OCl$_3$ | 26.53 | 0.9 | 70 | 30 |
| C$_6$H$_{11}$OCl$_3$ | 26.63 | 0.6 | 110 | 30 |
| C$_6$H$_{11}$OCl$_3$ | 26.69 | 0.4 | | |
| C$_6$H$_{11}$OCl$_3$ | 26.81 | 1.3 | 140 | 35 |
| C$_6$H$_{11}$OCl$_3$ | 27.80 | 20.0 | 95 | 30 |
| C$_6$H$_{11}$OCl$_3$ | 28.18 | 4.6 | >350 | 25 |
| C$_6$H$_{10}$OCl$_4$ | 28.48 | 1.8 | 18 | 10 |
| C$_6$H$_{10}$OCl$_4$ | 28.58 | 6.8 | >880 | 35 |
| C$_6$H$_{10}$OCl$_4$ | 28.86 | 29.4 | 5350 | 550 |

It is observed that, with respect to an extraction with tetrachloromethane, the extraction with 1,2,3-trichloropropane makes it possible to reduce the content of chloroaliphatic impurities by a factor of 2 to 25.

I claim:

1. A process for the production of epichlorohydrin starting from alyl chloride, to form a crude aqueous solution of dichloropropanols, a purification stage of the crude aqueous solution of dichloropropanols to remove chlorinated organic impurities by extraction by means of a recycled organic extraction solvent which is rich in 1,2,3-trichloropropane, said organic extraction solvent recycled from a distillation stage recovering and purifying 1,2,3-trichloropropane by-products produced during said pypochlorination stage in order to form a purified aqueous solution of dichloropropanols, and a dehydrochlorination stage of the purified solution of dichloropropanols to produce epichlorohydrin.

2. The process according to claim 1, wherein the recycled organic extraction solvent comprises at least approximately 50% by weight of 1,2,3-trichloropropane.

3. The process according to claim 1 comprising the following stages:

a) hypochlorination of allyl chloride to form a crude aqueous solution of dichloropropanols which additionally contains chlorinated organic impurities, including 1,2,3-trichloropropane and other chloroaliphatic impurities, including chloroaliphatic ethers and chloroaliphatic alcohols, b) extraction of this crude aqueous solution of dichloropropanols with a recycled organic extraction solvent, which is rich in 1,2,3-trichloropropane, in an amount sufficient to obtain an organic which mainly comprises 1,2,3-trichloropropane enriched in chloroaliphatic impurities and an aqueous phase containing the majority of the dichloropropanols, highly improverized chloroaliphatic impurities, c) dehydrochlorination of the dichloropropanols to epichlorohydrin by introduction of a basic compound into the aqueous phase obtained in stage b), steam distillation of the epichlorohydrin formed to obtain crude epichlorohydrin and discarding of the aqueous effluents, d) separation, by fractional distillation, of the crude dipichlorohydrin formed in c) into a light fraction, into an intermediate fraction consisting of purified eipchlorohydrin and into a residual heavy fraction, and recycling of the residual heavy fraction from this distillation to the extraction stage b) where it at least partially constitutes the recycled organic extraction solvent rich in 1,2,3-trichloropropane, e) washing of the organic phase obtained in stage b) with water to obtain, after separation of the phases, a washing water containing the majority of the dichloropropanols present in the said organic phase and a washed organic extract, containing markedly less dichloropropanols than as supplied, the washing water laden with dichloropropanols being recycled to at least one of the a) hypochlorination, b) extraction or c) dehydrochlorination stage, and f) separation, by fractional distillation, of the said washed organic extract from stage e) into a head cut conveyed to the separation stage d) of the crude eipchlorohydrin by distillation, into a middle cut consisting of purified 1,2,3-trichloropropane and into a bottom cut consisting essentially of the chloroaliphatic impurities.

4. The process according to claim 3, in which part of the purified 1,2,3-trichloropropane, corresponding to the middle cut obtained in the separation stage f) by distillation of the washed organic extract, is added to the residual heavy fraction obtained in the separation stage d) of the crude epichlorohydrin by distillation, the mixture obtained being recycled to the extraction stage b).

5. The process according to claim 3, in which the separation by distillation of the washed organic extract, carried out in stage f), is carried out such that the head cut conveyed to the separation stage d) of the epichlorohydrin by distillation contains from 50 to 98% of 1,2,3-trichloropropane.

6. The process according to claim 3, in which the extraction stage b) is carried out continuously with a ratio between the flow rate of the extraction solution rich in 1,2,3-trichloropropane and the flow rate of the crude aqueous solution of dichloropropanols which is greater than approximately 0.001 and less than approximately 0.1.

* * * * *

UNITED STATES PATENT AND TRADEMARK OFFICE
CERTIFICATE OF CORRECTION

PATENT NO. : 5,344,945
DATED : September 6, 1994
INVENTOR(S) : Frans Grunchard

It is certified that error appears in the above-indentified patent and that said Letters Patent is hereby corrected as shown below:

On the title page item [56], Under U.S. Patent Documents, the following should be inserted:

5,292,972 3/1994 John et al 568/847

Signed and Sealed this

Twenty-first Day of February, 1995

Attest:

BRUCE LEHMAN

*Attesting Officer*    *Commissioner of Patents and Trademarks*